US006656745B1

(12) United States Patent
Cole

(10) Patent No.: US 6,656,745 B1
(45) Date of Patent: Dec. 2, 2003

(54) DEVICES AND METHODS FOR A MULTI-LEVEL, SEMI-QUANTITATIVE IMMUNODIFFUSION ASSAY

(76) Inventor: Francis X. Cole, P.O. Box 517, Stow, MA (US) 01510

( * ) Notice: Subject to any disclaimer, the term of this patent is extended or adjusted under 35 U.S.C. 154(b) by 0 days.

(21) Appl. No.: 09/586,162

(22) Filed: Jun. 2, 2000

(51) Int. Cl.[7] ............................................. G01N 33/558
(52) U.S. Cl. ......................... 436/514; 422/56; 422/57; 422/58; 435/7.5; 435/970; 435/805; 435/810; 436/525; 436/530; 436/805; 436/810
(58) Field of Search ..................... 422/56–58; 435/7.5, 435/970, 805, 810; 436/514, 525, 530, 805, 810

(56) References Cited

U.S. PATENT DOCUMENTS

| | | | |
|---|---|---|---|
| 4,200,690 A | 4/1980 | Root et al. | |
| 4,246,339 A | 1/1981 | Cole et al. | |
| 4,407,943 A | 10/1983 | Cole et al. | |
| 4,632,901 A | 12/1986 | Valkirs et al. | |
| 4,703,017 A | 10/1987 | Campbell et al. | |
| 4,879,215 A | 11/1989 | Weng et al. | |
| 4,883,688 A | 11/1989 | Houts et al. | |
| 4,945,205 A | 7/1990 | Litman et al. | |
| 4,956,302 A | 9/1990 | Gordon et al. | |
| 4,960,691 A | 10/1990 | Gordon et al. | |
| 5,073,484 A | 12/1991 | Swanson et al. | |
| 5,081,013 A | * 1/1992 | Rovelli et al. | 435/7.92 |
| 5,120,643 A | 6/1992 | Ching et al. | |
| 5,401,667 A | * 3/1995 | Koike | 436/514 |
| 5,409,664 A | * 4/1995 | Allen | 422/56 |
| 5,458,852 A | 10/1995 | Buechler | |
| 5,559,041 A | * 9/1996 | Kang et al. | 436/518 |
| 5,654,162 A | 8/1997 | Guire et al. | |
| 5,756,362 A | 5/1998 | Durst et al. | |
| 5,922,615 A | 7/1999 | Nowakowski et al. | |
| 6,306,642 B1 | * 10/2001 | Nelson et al. | 435/287.1 |

* cited by examiner

Primary Examiner—Christopher L. Chin
(74) Attorney, Agent, or Firm—Wolf, Greenfield & Sacks, P.C.

(57) ABSTRACT

The present invention relates to an immunoassay device featuring a semi-quantitative, multi-level method for determining the presence and an amount of an analyte. The immunoassay involves a device comprising a layer with a porous medium deposited thereon. The device has several binding zones in which each zone comprises a defined amount of a binding reagent to bind and immobilize the analyte. The present invention also features an inscribed capillary channel having fluid barriers that allow control of a rate of migration of fluid along the porous medium. The device typically provides at least some of the binding zones within the capillary channels such that a solvent quickly traverses through the capillary channels and provides a semi-quantitative result. Preferably, any binding of an analyte is accompanied by a visual change in the binding zone such that one can easily detect visually an amount of analyte present in the sample. The invention also features a method for determining the presence and amount of an analyte. The invention also features a device for facilitating removal of liquids and/or preventing back flow along a porous medium comprising a series of capillary channels in parallel arrangement with each other in which each of the capillary channels are contiguous with the fluid pathway. The invention also relates to a method for making an immunoassay device comprising providing a layer of a continuous porous medium and etching the medium to provide fluid barriers, at least a portion of which define a capillary channel.

39 Claims, 6 Drawing Sheets

DEVICES AND METHODS FOR A MULTI-LEVEL, SEMI-QUANTITATIVE IMMUNODIFFUSION ASSAY

FIELD OF INVENTION

The present invention relates to a device for determining the presence and amount of an analyte via immunodiffusion assay techniques. The device features multiple binding zones and capillary channels to maintain uniform fluid flow. By these arrangements, the device allows detection of analyte concentration at multiple, pre-defined threshold levels. The invention also relates to a novel reservoir zone comprising a network of capillary channels. Methods for preparing the device and for determining the presence and amount of an analyte are also described herein.

BACKGROUND OF THE INVENTION

Immunodiffusion techniques are found in a wide variety of applications including medical diagnosis. Generally, such techniques involve screening for the presence of an analyte by diffusing a solution suspected of containing the analyte through a solid support. Bound to the support is a binding agent which is a specific receptor for the analyte. An analyte contained in the sample eventually reacts with the immobilized binding agent. A reaction between the binding agent and analyte can be detected by a variety of indicators. For example, sandwich immunoassay techniques involve the formation of a three member complex of binding agent-analyte-label, and formation of the complex can be determined via visual, radioactive, spectroscopic, or other methods.

Immunodiffusion techniques can be useful in analyzing a large number of biological components, including antibodies, proteins, enzymes and nucleic acids, depending on the particular binding agents employed. For example, where the analyte is an antigen, typical binding agents are antibodies, and vice versa.

Many specific immunoassay methods have been reported.

U.S. Pat. No. 4,960,691 (Gordon et al.) describes a chromatographic test strip having a site for immobilizing an analyte. The site contains a reagent capable of reacting with the analyte and immobilizing it. Another diffusable reagent is bound upstream of this site that is capable of binding with the analyte-immobilized reagent couple. This other reagent may be a labeled material which can be detectable upon reaction with the couple.

U.S. Pat. No. 4,879,215 (Weng et al.) is directed to a method and device for determining the presence of an analyte and amounts of the analyte. Weng et al. describes the formation of a detectable signal which can relate to an amount of analyte present in the test solution. The detectable signal is formed by contacting a test strip having been traversed by a test solution with a developer solution containing components of a signal producing system. The detectable signal is compared to a control signal to determine an amount of the analyte.

U.S. Pat. No. 4,703,017 (Campbell et al.) is directed to a solid phase assay involving an antibody supported on a solid phase support. The antibody is capable of binding an analyte, typically a hapten or antigen. After contacting the solid support with a sample suspected of containing an analyte, any antibody that remains unbound by an analyte is contacted with a tracer. The bound tracer can be viewed visibly without the aid of instrumentation. A test for hCG (pregnancy test) which is a simple yes/no at a single level of analyte is described.

U.S. Pat. No. 5,073,484 (Swanson et al.) is directed to a method and apparatus for quantitatively determining an amount of an analyte involving a liquid-permeable solid medium having a number of reaction zones. One embodiment of Swanson employs a filter paper strip having a series of reaction zones separated from each other by spacer layers. Swanson describes preparing the strip by binding a reactant to individual rectangular pieces of filter paper and alternately attaching these pieces with similar pieces of filter paper that do not contain a reactant. This results in portions of a fluid pathway which are discontinuous, due to an interface between one piece of filter paper and an adjacent piece of filter paper.

U.S. Pat. No. 5,756,362 (Durst et al.) discusses the use of capillary action to aid the assay process. The capillarity described therein is that inherent in microporous solid phase material which is known to be non-uniform in nature. To determine different concentration levels, a number of strips each having a measurement zone with a different concentration of a binding reagent is employed.

U.S. Pat. No. 5,458,852 (Buechler) details the difficulties of reliance on the capillarity of porous matrices in assay devices. Buechler discloses a non-porous medium which requires precision parts, aligned grooves and plasma treatment to graft functional groups to create hydrophilic surfaces for these devices. Such a requirement adds to the complexity and cost of manufacture of the assay device.

While many assay techniques exist, there remains a need to develop immunoassay techniques and products. If such techniques are to be used by the general public, ideally the methods should be user-friendly, and capable of being mass-produced in an inexpensive manner.

SUMMARY OF THE INVENTION

One aspect of the present invention provides a device for determining the presence of an analyte. The device comprises a layer including a continuous porous medium deposited thereon and a fluid pathway as defined by fluid barriers in the porous medium. At least a portion of the barriers define a capillary channel. The device also comprises an analysis zone within the fluid pathway comprising a plurality of binding zones for binding and immobilizing the analyte. Each binding zone is defined by a concentration of a binding reagent immobilized on the medium.

Another aspect of the invention provides a method for determining the presence of an analyte. The method involves applying a sample suspected of containing the analyte to an application zone positioned at a first end of a layer of a porous medium. The sample is allowed to travel through a plurality of binding zones and a capillary channel, each binding zone comprising a concentration of immobilized binding reagent and the capillary channel comprising fluid barriers in the porous medium. The method also involves detecting a number of binding zones that have undergone a binding event between the binding reagent and the analyte. The method further comprises determining an amount of analyte based on the number of binding zones that have undergone a binding event.

Another aspect of the present invention provides a method for making an immunoassay device comprising providing a layer comprising a continuous porous medium deposited thereon and etching the medium to provide fluid barriers in the porous medium. At least a portion of the barriers define a capillary channel. The method further comprises depositing a plurality of binding zones within the fluid barriers, each binding zone being defined by a concentration of binding reagent immobilized on the medium.

Another aspect of the present invention provides a device for facilitating removal of fluids, comprising a fluid pathway defined within a layer of a porous medium. The device also comprises a reservoir positioned at a terminal end of the pathway, the reservoir comprising a series of capillary channels inscribed in the porous medium. Each of the channels are adjacent at least one other channel and each capillary channel is contiguous with the fluid pathway.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION

Figure 1:
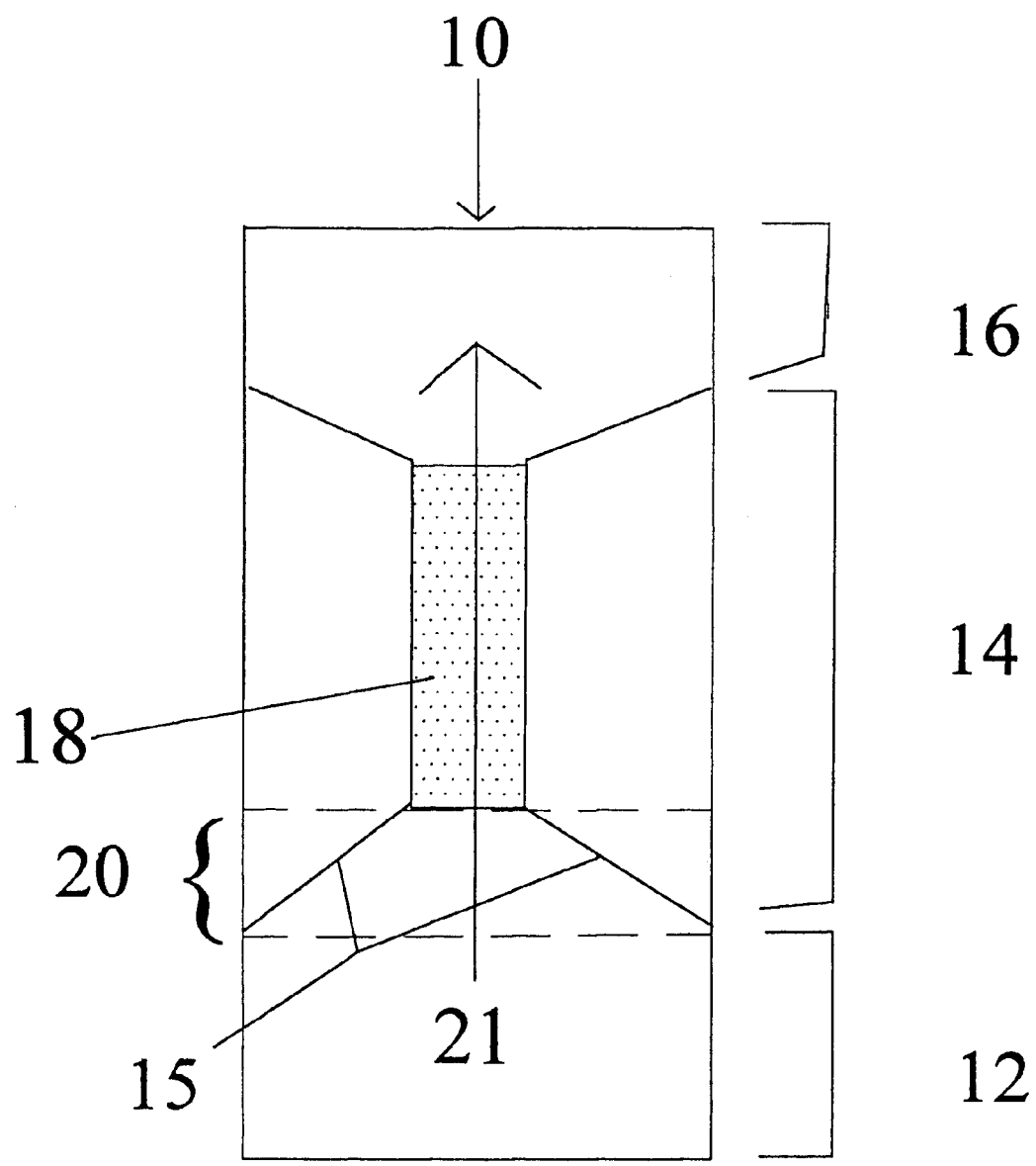
FIG. 1 shows a top view of a test strip of the present invention featuring a capillary channel and an application zone which constricts to the channel.

The present invention features a multi-level, quantitative immunodiffusion assay device having fluid flow controlled by capillary channels inscribed in a porous medium. This and other devices of the invention can be used to detect the presence and amount of a variety of analytes, and this aspect of the invention has advantages over certain prior art qualitative tests which indicate merely the presence of an analyte. Typical examples of such qualitative tests in commercial use include the well known pregnancy tests and screening tests for drug abuse. For such medical diagnostic tests, the multi-level semi-quantitative capability of present invention provides the advantageous feature of determining the presence of an analyte as well as providing information as to the progress or extent of a medical condition.

In addition to the semi-quantitative capabilities, the present invention features the use of capillarity control via fluid barrier lanes in the support medium to direct and control fluid diffusion through the support. A more uniform fluid flow can provide precise and reliable data. The use of a capillary channel defined by fluid barrier lanes coupled with a multi-level assay presents an improvement over test strips of the prior art.

It is an advantageous feature of the present invention that an easily detectable system for semi-quantitative analysis in combination with the rapidity and uniform flow provided by a capillary channel is provided. The present invention can be made and used via relatively inexpensive methods.

Thus, one aspect of the present invention provides a device for determining the presence of an analyte. In this aspect, the device comprises a layer, or substrate including a continuous porous medium deposited thereon. "Porous medium" refers to any medium that is capable of allowing fluid diffusion. The advantages of porous media include: (1) a large internal surface area available for binding specific binding agents, and hence a capability to detect trace quantities of analyte; and (2) an efficient and simple method of rinsing away undesirable substances (inhibitors and unbound label). Fluid is drawn through porous media by capillary forces provided by interconnecting pores. Such forces are a function of (among others) overall dimensions of the medium, the size and distribution of pores, and the nature of and distribution of solids in the medium.

In this aspect of the present invention, a fluid pathway is defined by fluid barriers in the porous medium. The "fluid" comprises a solvent that is capable of carrying the analyte and other reagents through the porous medium along the fluid pathway. The fluid barriers typically comprise two opposing barriers which run substantially parallel with each other, the barriers encompassing a lane in the porous medium which is the fluid pathway. Thus, fluid barriers can restrict fluid flow to a defined fluid pathway. In one embodiment, fluid barriers are a construct in the medium to prevent flow of fluid from one side of the barrier to the other, i.e. the barrier is liquid impermeable. In one embodiment, a barrier can be a region in the layer free of the porous medium, e.g., formed by etching the medium, either by chemical etching or by laser etching. Alternatively, the region free of the porous medium can be replaced with a non-porous substance, or any other substance that prevents fluid diffusion. In another embodiment, the fluid barriers can be formed by depositing a solid structure on the medium such that flow is restricted through the solid barrier, e.g. as formed by screen printing. In another embodiment, the fluid barriers are defined by edges of the layer itself. Edges can be formed by slicing away portions of the layer, for example, by cutting the layer with scissors, a steel-ruled die, or a laser.

In one embodiment, the fluid barriers can be serrated. In many instances, fluid flow rate along an edge can be greater than the flow rate along the middle of the lane (i.e., fluid pathway). Thus, in this embodiment, any non-uniformity in flow rate along an edge of the barrier versus that in the middle of the lane can be compensated by providing serration along the edges (i.e., serrated barriers). The extent of serration can be varied to control the flow rate along the edge of the lane. For example, the number of serrated units per unit length can be increased or decreased, and the height of each serrated unit can be varied.

Also in this aspect of the invention, at least a portion of the barriers can define a capillary channel. "Capillary channel" as used herein refers to a channel that is capable of transporting fluid via wetting forces and interfacial surface tension, as known by those of ordinary skill in the art. The capillary channel of the present invention is defined by fluid barriers in which interfacial surface tension at a barrier edge can be used to control fluid flow. Thus, "capillary channels" of the present invention are inscribed in or on the porous medium and are to be distinguished from capillary flow that occurs through voids and cavities inherent in porous media. In one embodiment, the channels are sufficiently narrow so as to regulate bulk flow of fluid. In one embodiment, the capillary channel has a width of less than about 4 mm, more preferably less than about 3 mm, and even more preferably less than about 2 mm. In one embodiment, the barriers comprise two barriers which run parallel to each other and the entire fluid pathway comprises a capillary channel. In another embodiment, a portion of the barriers define a capillary channel. For example, a sample can be applied at one end of a fluid pathway which is not a capillary channel, i.e., has a large width and fluid transport is driven solely by the capillarity of the porous matrix. As the sample progresses along the pathway, the pathway may constrict to a capillary channel by which capillary forces act to speed up flow rate. Thus, the capillary channel controls rate of fluid flow.

In one set of embodiments, the device further comprises an analysis zone within the fluid pathway. In one embodiment, the analysis zone is defined by a length along the fluid pathway spanning a plurality of binding zones. A "binding zone" is defined by a region of the medium including a binding reagent immobilized on the medium, preferably at a specific concentration. The "binding reagent" is capable of specifically binding an analyte, typically to the exclusion of other species or potential species in the sample although other minor binding events may occur. Examples of analytes include a variety of biological components, including antibodies, proteins, enzymes and nucleic acids. For example, if the analyte is an antigen, the binding reagent would typically be an antibody, and vice versa. The analyte can be DNA in which the binding agent comprises complementary DNA, and this assay can have applications in gene screening and DNA sequencing.

A concentration of binding reagent is an amount of binding agent per unit volume of support medium, and this concentration determines a sensitivity of a given binding zone. In one embodiment, the concentration of binding reagent immobilized on the medium defines a maximum threshold detection level.

The plurality of binding zones provides the semi-quantitative detection capability in the present invention, i.e., a multi-level immunoassay technique, in which the number of levels is determined by the number of binding zones. Individual binding zones can be reactive for pre-determined levels of analyte in a sample, i.e., each binding zone has a specified concentration of binding reagent. In addition, each binding zone has a threshold signal level, depending on the method of detection used. In one embodiment, the plurality of binding zones is arranged substantially linearly and sequentially with respect to a direction of fluid flow. In this embodiment, as the sample diffuses through the fluid pathway, a certain amount of analyte will bind to the binding reagent in a first binding zone. If an amount of analyte in the sample is greater than the amount of binding reagent in the first binding zone, the fluid sample that reaches the second binding zone (which is downstream of the first binding zone) will have excess analyte to react with binding reagent in the second binding zone. By determining the number of binding zones that have participated in a "binding event" (i.e., a reaction between a binding reagent and an analyte), a threshold amount of analyte present in the sample can be determined. In this example, the amount of analyte in the sample is at least greater than the threshold amount pre-determined for the first binding zone, and the presence of a detectable signal from the second binding zone will determine whether the amount of sample is greater or less than the threshold amount pre-determined for the second binding zone.

In one embodiment, the concentration of binding agent in the binding zones can decrease successively in the direction of fluid flow, i.e. the first binding zone can contain a high concentration of binding reagent to remove the majority of analyte in the sample. Subsequent binding zones can have successively lower concentrations to provide the threshold levels desired. In another embodiment, each binding zone has an equal concentration of binding reagent. In this embodiment, each binding zone can contain binding reagent having different affinities for binding the analyte. In one embodiment, a first binding zone can contain a binding reagent having a strong affinity for the analyte whereas successive binding zones can have decreasingly lesser affinities for the analyte.

In one embodiment, the concentration of binding reagent in the first zone is adjusted so that a detectable signal occurs at a low analyte level. It is often desirable that this be the minimum detection level achievable with that binding agent. The concentration of analyte in the fluid sample emerging from the first binding zone is reduced by the amount of analyte bound therein. The fluid sample is then funneled into zone two. In one embodiment, the concentration of binding agent in zone two is adjusted to be at or below the binder concentration in zone one and is capable of producing a detectable reaction signal if sufficient analyte is bound at that zone. The dimensions of zone two can be adjusted by immobilizing a binder concentration sufficient to provide the desired threshold detection. Depending on the amount of bound analyte in zone two, fluid emerging from this zone can carry a remaining amount of analyte to be bound in the next zone.

In one embodiment where it is desired to test for analyte over a broad range of concentration (e.g., one or more orders of magnitude) and it is difficult or impossible to achieve the desired threshold levels by merely adjusting the dimensions or binding affinity of the binding zones, other binding regions are interspersed between the threshold sensitive binding zones. These binding regions are referred to as "adjuster zones". If, for example, both a small and very large quantity of analyte is to be detected, binding zone 1 can have a low concentration of binding reagent immobilized thereon. An adjuster zone containing a defined concentration of binding reagent can be disposed between binding zone 1 and binding zone 2 to "filter out" a defined amount of analyte as the sample flows from binding zone 1 to binding zone 2. To prevent confusion from binding zones that are used for analysis and/or detection purposes (also referred herein as "detection zones"), the adjuster zones may be hidden from view, e.g., by means of an overlaying mask. Alternatively, the adjuster zone may be free of any visible detection markers, or the user can be instructed to ignore the readings of the adjuster zones.

In one embodiment, at least one of the binding zones is positioned within the capillary channel. By this arrangement the advantageous effects of the capillary channel can be exploited to transport the sample through the plurality of binding zones. Preferably, more than one of the binding zones is positioned within the capillary channel and the capillary channel controls the rate of fluid flow through the binding zone. For example, one of the binding zones can be positioned outside of the capillary channel upstream of the other binding zones in the capillary channel. The first binding zone can contain the highest concentration and/or amount of binding reagent to filter out a majority of the analyte, and the binding zones within the capillary will provide a more sensitive threshold semi-quantitative analysis.

In one embodiment, the device further comprises a "control binding zone". The control binding zone is typically positioned at or near the end of the capillary channel. The control binding zone can provide a reliable test which indicates whether the device is operable, i.e., it is capable of reacting with the analyte. For example, a control sample of analyte can be positioned upstream of the control binding zone, for example near the application zone. The control analyte will redissolve once a fluid has been applied to the application zone and the control analyte traverses along the parallel fluid pathway to bind with a control zone. If the control zone does not undergo a detectable change, a user will know that the device is not operating properly. In one embodiment, the control zone is located within a lane other than the sampling lane.

In one embodiment, the device contains at least three binding zones. A three-binding zone device is also referred to as a "tri-level test". The number of levels can be tailored, in combination with the concentration of binding reagents, to alter the sensitivity of the semiquantitative analysis depending on the particular application or desired precision. Because the device also detects the presence or absence of an analyte, the device can also be referred to as a "yes/no/multi-level" test. For example, the device can be used to screen for the detection and progress of a particular medical condition, e.g. one threshold level can indicate that the condition is at a preliminary stage, whereas another threshold amount can indicate that the condition is in an advanced state.

One example of such a medical diagnosis test is one that screens for prostrate cancer. The occurrence of prostate cancer in men is based upon the detection of prostate specific antigen (PSA) in body fluids. The condition is quite common and in the U.S. almost all men over the age of fifty can be expected to have detectable levels of PSA in their blood. Low levels of PSA do not necessarily call for medical intervention. However, higher levels of PSA may indicate the need for biopsy and potentially for pharmaceutical or radiation treatment, or even surgical intervention. In such a situation, a multilevel, qualitative test poised to give yes/no responses at trace levels, at the threshold for treatment, and at the level indicative of surgical intervention is clearly beneficial.

Similarly in the assessment of pregnancy, a multi-level test for the detection of the pregnancy hormone hCG (human Chorionic Gonadotropin) can serve to assess the progress of the pregnancy i.e. first few days, first week, or advanced. Such a pregnancy test would be of general utility. For example, one use would involve assessing a potentially dangerous ectopic pregnancy.

FIG. 1 shows a top view of a test strip of the present invention. Test strip 10 comprises an application zone 12 positioned on one end of strip 10, a reservoir zone 16 positioned in an end of strip 10 opposite that of application zone 12, and an analysis zone 14 positioned intermediate application zone 12 and reservoir zone 16 in strip 10. Application zone 12 originates a fluid pathway as test strip 10 initially contacts a sample via application zone 12. Analysis zone 14 and reservoir zone 16 are also located within the fluid pathway in which application zone 12 and reservoir zone 16 define a length of the fluid pathway. The fluid pathway is bound widthwise by fluid barriers 15. A portion of fluid barriers 15 narrows to define a capillary channel 18. In the embodiment of FIG. 1, capillary channel 18 does not span the entire length of the strip but rather application zone 12 constricts into capillary channel 18. This constriction occurs in constriction region 20. One advantage of this embodiment is that a large amount of sample can initially contact test strip 10, and upon reaching capillary channel 18, capillary forces can urge the sample rapidly and uniformly through the fluid pathway having a direction shown by arrow 21. It is understood that FIG. 1 indicates a general region of the application zone 12, analysis zone 14 or reservoir zone 16, as indicated by the regions bound by brackets, and FIG. 1 does not strictly confines these zones to the regions bound by the brackets. There can be some overlap between the zones, as readily understood by those of ordinary skill in the art.

Figure 2:
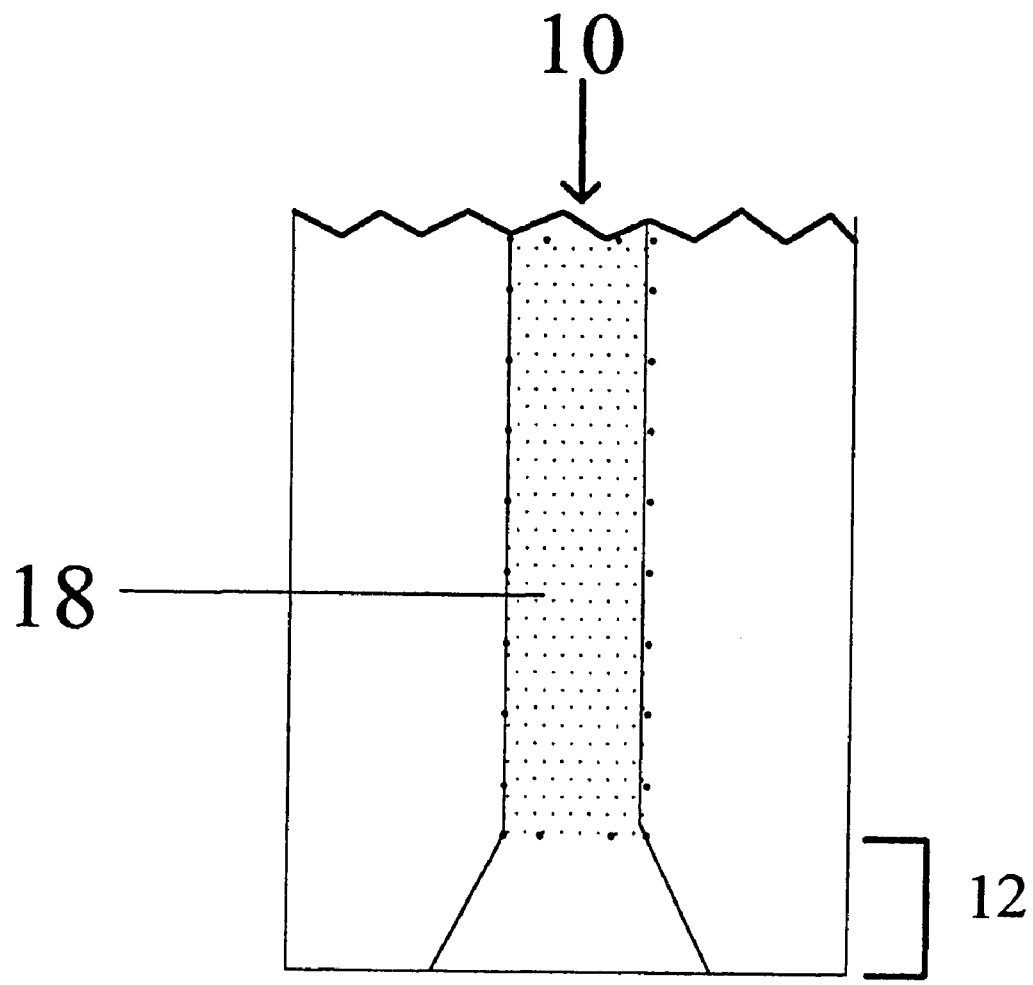
FIG. 2 shows a top view of a cutaway bottom portion of a test strip of the present invention, featuring a tapered region leading to the capillary channel.
Figure 3:
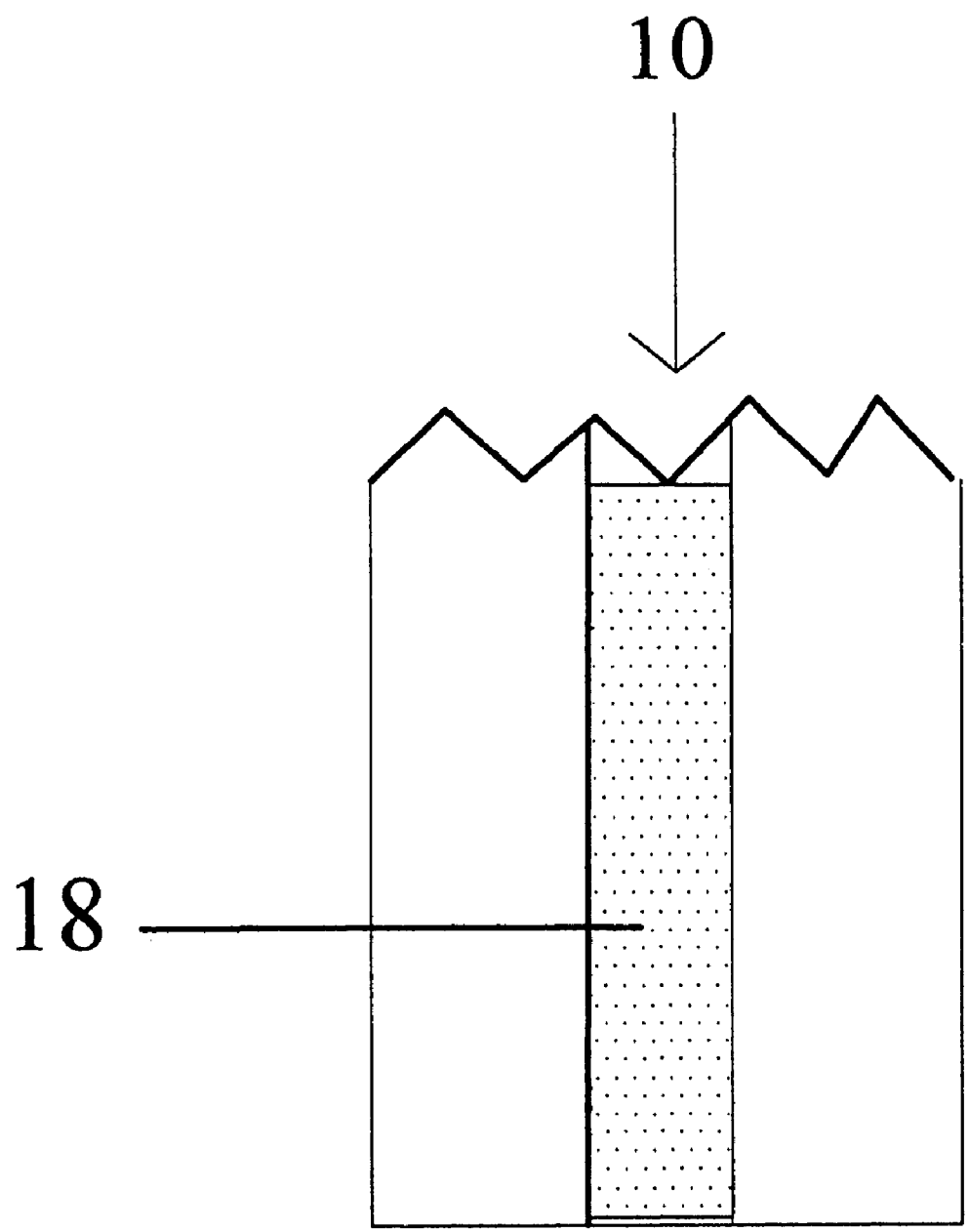
FIG. 3 shows a top view of a cutaway bottom portion of a test strip of the present invention, featuring a capillary channel that extends to the application zone.

FIG. 2 shows a top view of a cutaway portion of test strip 10, featuring a tapered constriction region from the application zone 12 to capillary channel 18. The type of constriction zone, or absence or presence of the constriction zone is not a limiting factor of the invention and one of ordinary skill in the art can tailor the type of constriction that best optimizes the immunoassay procedure. FIG. 3 shows yet another embodiment of test strip 10, via a top view cutaway portion of test strip 10 in which there is no constriction region. FIG. 3 shows the entire fluid pathway bound by capillary channel 18.

Figure 4:
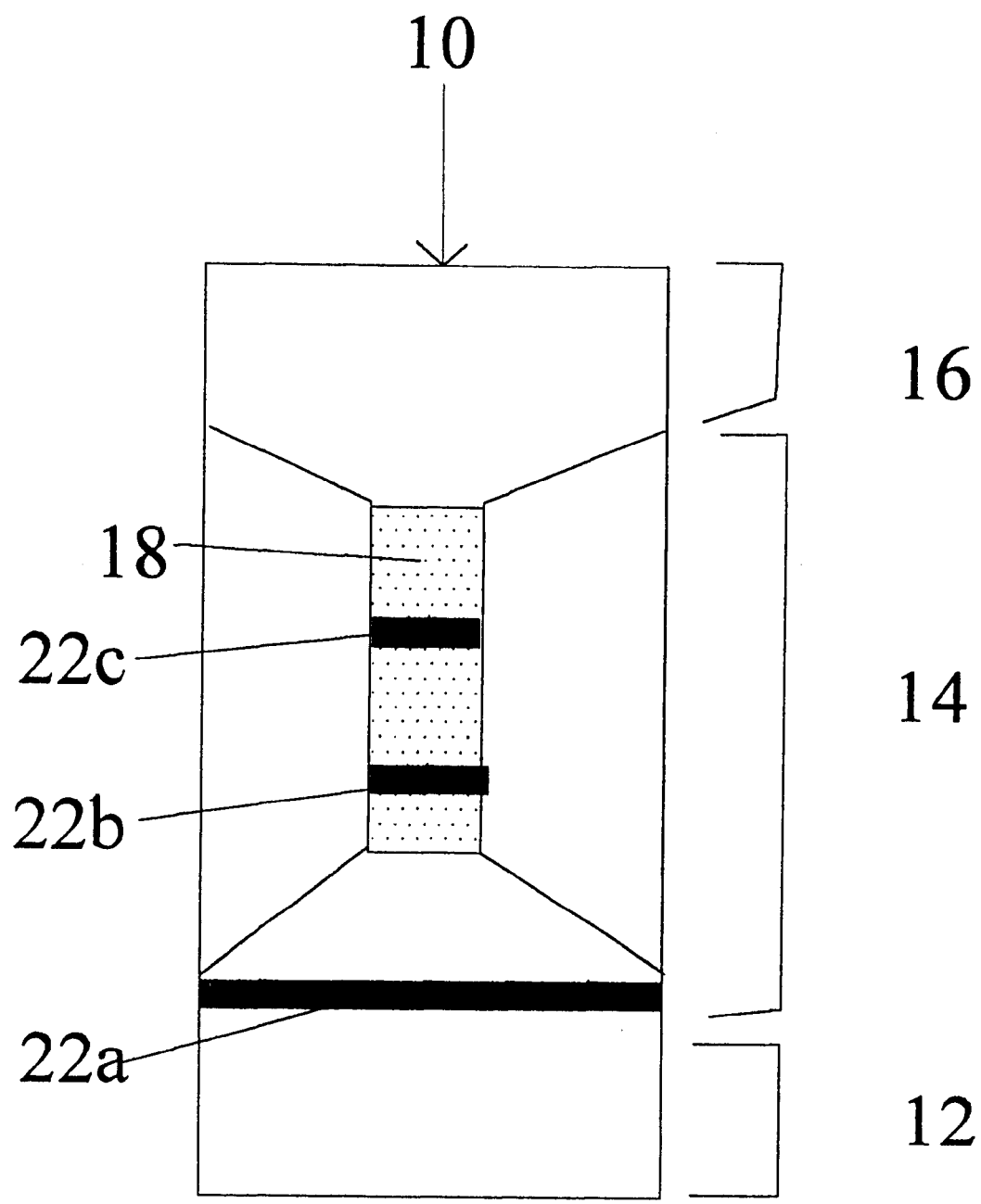
FIG. 4 shows a top view of a test strip of the present invention, featuring multiple binding zones.

FIG. 4 shows a top view of test strip 10 featuring analysis zone 14 as defined by a plurality of binding zones 22a–c. FIG. 4 features the embodiment in which at least one of the binding zones, i.e., binding zones 22b and 22c, is positioned within capillary region 18. This example also features an initial binding zone 22a which has a larger amount of binding reagent (as indicated by a larger area spanned by the binding reagent). This arrangement allows a large amount of sample to contact test strip 10 at application zone 12 whereby binding zone 22a can remove or bind most of the analyte present in solution. Binding zones 22b and 22c can feature smaller amounts of binding reagents to provide threshold levels of considerably elevated analyte levels. Of course, in other embodiments, a varying the amounts of binding reagent in each binding zone can be effected by varying the concentration of binding reagent, i.e. changing the amount per unit volume.

Reservoir zone 16 facilitates removal of fluid from the analysis zone 14. In one embodiment, reservoir zone 16 can comprise an absorbent pad to "mop up" any excess fluid that passes through the analysis zone 14. Reservoir 16 is also useful for preventing back flow of sample into the analysis zone which can mar the analysis.

Another aspect of the invention provides a device for facilitating removal of fluids, particularly removal of fluids from an immunoassay device. The device comprises a fluid pathway and a reservoir positioned at a terminal end of the pathway. The reservoir comprises a series of capillary channels in which each of the channels are adjacent with at least one other capillary channel. Each capillary channel is inscribed in the porous medium and is contiguous with the fluid pathway. This is an advantageous feature in that capillary forces are used to urge fluid flow away from the analysis zone in an effective manner that does not depend on absorbency of a pad or effective contact between an absorbent pad and the medium. In addition, the device can be used to prevent back flow of fluid towards the analysis zone.

Figure 5:
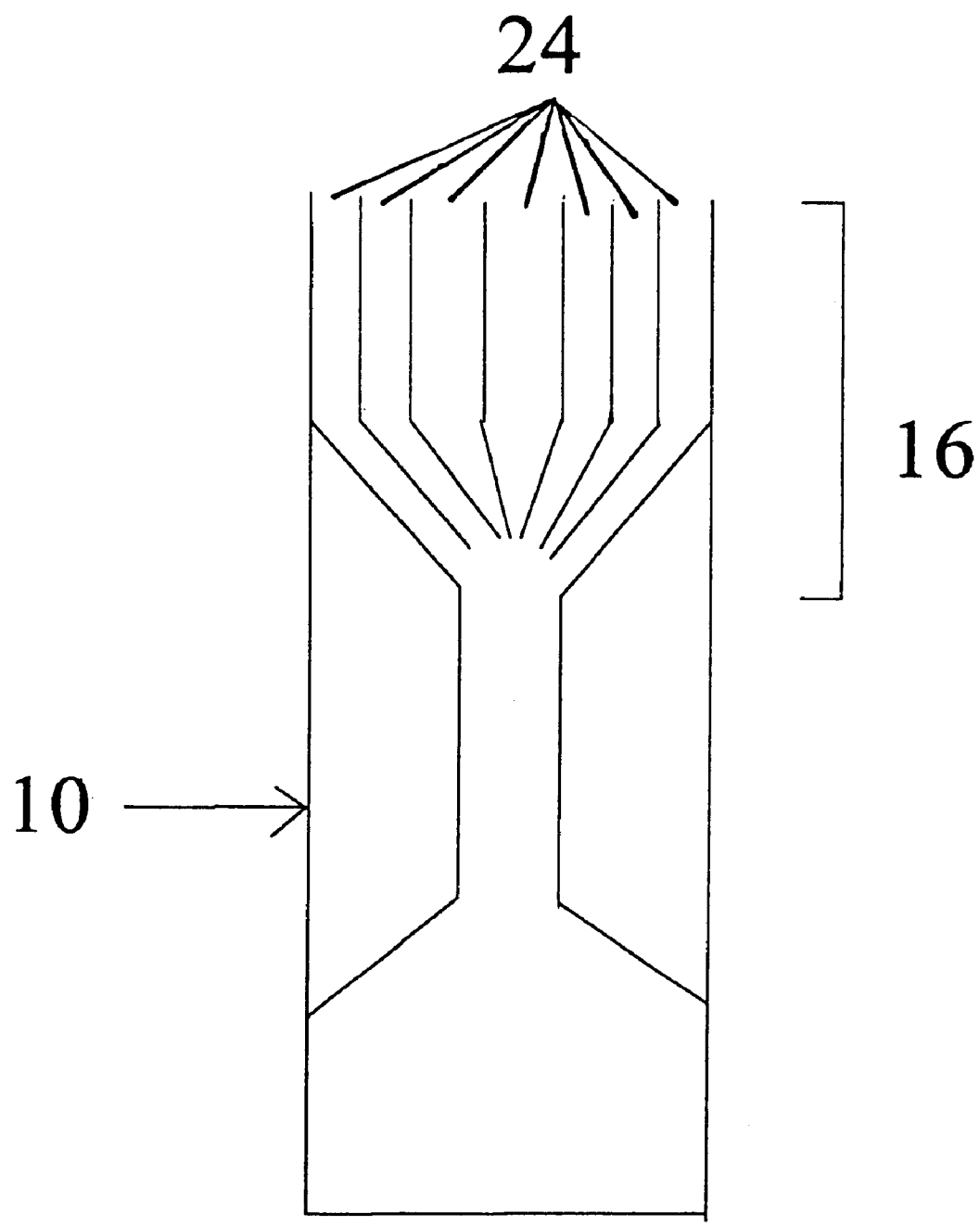
FIG. 5 shows a top view of a test strip of the present invention, featuring a reservoir zone comprising a series of capillary channels.

FIG. 5 shows a top view of a test strip 10 containing reservoir 16 comprising a plurality of inscribed capillary channels 24 adjacent at least one other channel (e.g. FIG. 5 shows inner channels adjacent and disposed between two other channels whereas outer channels are adjacent only one other channel). The capillary channels can be inscribed by any method used to prepare fluid barriers 15. In addition, each capillary channel 24 is contiguous with a fluid pathway, i.e., the fluid pathway is continuous through capillary channels 24. Of course, this reservoir is not limited to use with the immunoassay device of the present invention and can be used in conjunction with any device for the analysis of binding pairs by using a porous medium, as is known in the art.

Figure 6:
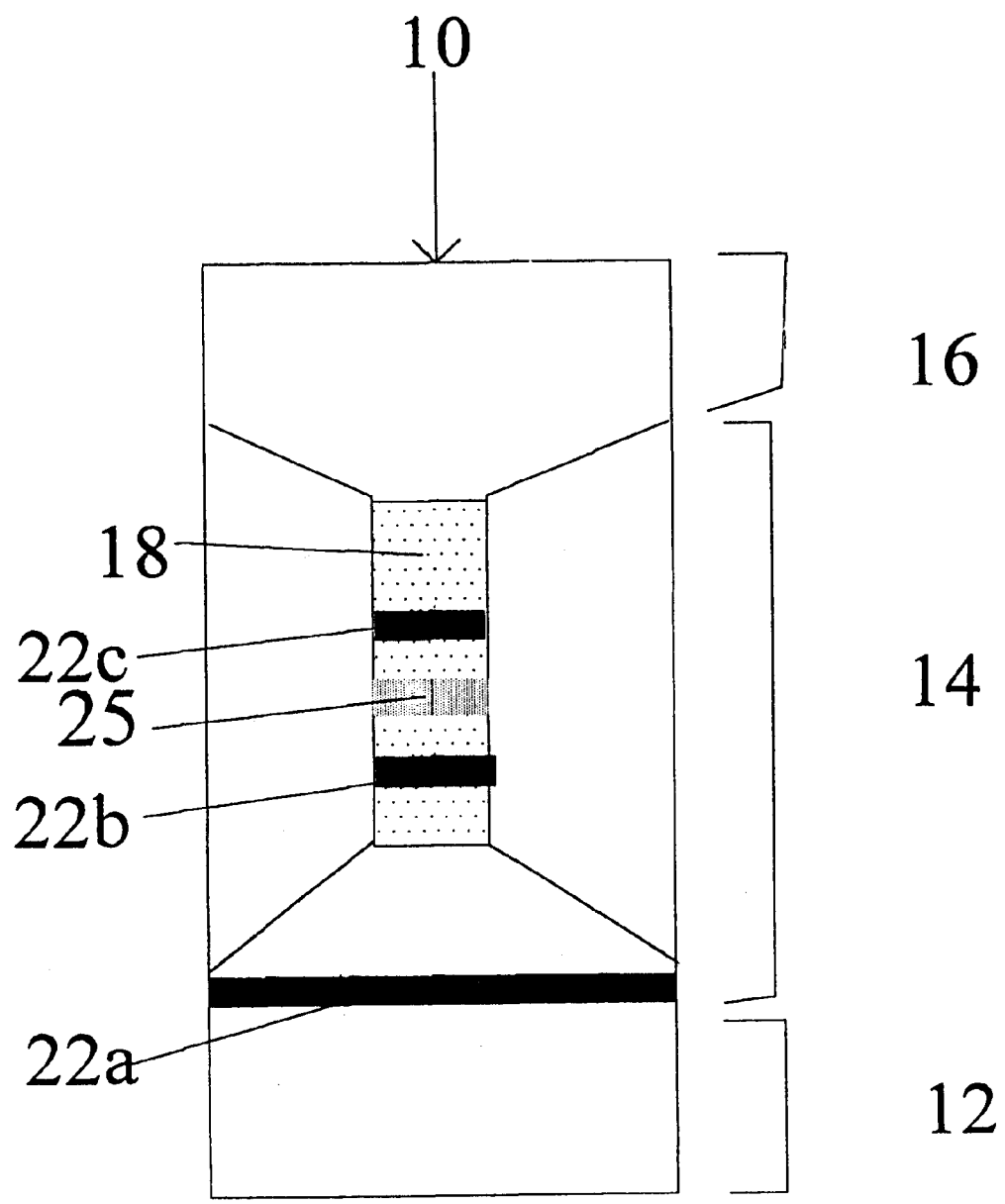
FIG. 6 shows a top view of a test strip of the present invention, featuring an adjuster zone between two detection zones.

FIG. 6 shows a top view of a test strip 10 featuring an adjuster zone 25 positioned between binding zones (i.e. detection zones) 22b and 22c. This adjuster zone may be masked over to avoid confusion. In any case, this zone allows the threshold level of binding zone 22c to be set at a higher analyte level than might otherwise be achievable.

Porous Media

The use of porous media, particularly microporous media for conducting assays to detect analytes has many advantages over non-porous media, and various types of porous media can be applied in the present invention, as known by one of ordinary skill in the art. In one embodiment, the porous medium has a thickness of about 10 $\mu$m to about 400 $\mu$m, and more preferably a thickness from about 100 $\mu$m to about 200 $\mu$m. In one embodiment, the porous medium includes pores having a mean average diameter from about 0.45 $\mu$m to about 50 $\mu$m. Examples of porous media that can be used for the present invention include natural, synthetic, or naturally occurring solid phase material that are synthetically modified. Specific examples include papers (fibrous) or membranes (microporous) of cellulose materials such as paper, cellulose, and cellulose derivatives such as cellulose acetate and nitrocellulose; olefin or thermoplastic materials including films of polyvinyl chloride, polyethylene, polyvinyl acetate, polyamide, polycarbonate, polystyrene, and the like. In one embodiment, the porous medium is nitrocellulose.

Application Zone

In one embodiment, the device of the present invention includes an application zone at a first end of the fluid pathway, where fluid flow is initiated. The application zone is positioned prior to the analysis zone and can include a wick for receiving the sample. The wick can be an absorbent pad layered on top of the medium at a first end of the fluid pathway. The wick can serve as a bridge between the fluid sample and the strip. This wick may also serve as a pre-filter for removing undesirable particulate matter. The wick may have dispersed within it appropriate reagents to buffer or otherwise condition the sample in a manner so as to optimize test performance.

A readily dispersible labeling agent for detecting the bound analyte species may be positioned in the application zone between the wick and the analysis zone. The labeling agent can be provided in dry form on a pad. Various labeling agents are known in the art: radioactive labels, fluorescent labels, or any other label by which the bound analyte can be detected either visually (i.e. a visual labeling agent, for example colloidal gold) or by instrumentation methods (e.g. radioactive detection methods, spectroscopic detection methods, etc.). The label can be provided as a "conjugate pad" and layered on the application zone. The function of this pad is simply to hold the dried label prior to use and to allow facile dissolution. The label can also be dissolved in a certain volume of sample so as to affix an amount of label reacting with a given total of analyte. In the case of a visible label, it should dissolve rapidly and travel downstream in a tight band with minimal tailing. Such tailing is undesirable because it may increase a total mass of analyte which can react with label, resulting in highly sensitive deviations in flow rate.

Another aspect of the present invention provides a method for determining the presence of an analyte. Prior art methods include lateral flow immunodiffusion techniques in which a test sample is added to a porous medium and allowed to migrate in a linear or longitudinal fashion through a binding zone containing a non-diffusively bound specific binding agent. The sample then flows to a reservoir zone. Liquid migration occurs in a direction transverse to the porous matrix. Immunochromatography is a modification of the lateral flow technique in which the amount of test analyte is deduced from the distance traveled in the binding zone.

In a prior art generalized laboratory immunoassay format, a precisely measured quantity of test sample is combined with defined amounts of test reagents. The procedure may involve carefully timed sequential mixing, incubation, and washing steps where undesired elements are rinsed away.

This aspect of the invention provides an advantageously simpler method for semiquantitatively determining the presence and amount of an analyte. The invention comprises the steps of providing a device, such as the device described previously. The method further involves applying a sample suspected of containing the analyte to an application zone positioned at a first end of a layer of a porous medium, and allowing the sample to travel through a plurality of binding zones and a capillary channel. Each binding zone comprises a concentration of immobilized binding reagent. The capillary channel comprises fluid barriers in the porous medium. In one embodiment, the fluid barriers comprise etched barriers in the porous medium. The method also involves detecting a number of binding zones that have undergone a binding event between the binding reagent and the analyte. "Detecting" can occur either visually or by instrumentation methods. The species detected typically comprises a binding reagent-analyte couple bound to a labeling agent (sandwich immunoassay). Finally the method involves determining an amount of analyte based on the number of binding zones that have undergone a binding event. This "determining" is a semiquantitative method in that a threshold amount of analyte can be determined, based on an amount of binding reagent immobilized in the medium.

In other embodiments, the method can further comprise any one or any combination of the following steps: (1) pre-filtration of the sample; (2) mixing of the sample with a labeling agent (this can occur either on the strip, e.g. binding a labeling agent on the application zone, as described above); (3) a timed incubation (this step can occur as the sample migrates through the application, detection and reservoir zones and the sample can be allowed to incubate for additional periods of time after migration); and (4) washing the unbound labeling agent (this step can reduce errors resulting from inadvertent streaking, or other unwanted processes).

An advantageous feature of the method is the ease of operation, providing little opportunity for operator error. Untrained operators can perform such tests as the test can require the operator to perform a single process, i.e. adding the sample. Thus, the untrained operator can have considerable confidence in the accuracy of the result obtained without having to worry whether numerous steps were carried out properly. For example, the test of the present invention allows performing "at home" pregnancy testing.

Another aspect of the present invention provides a method for making an immunoassay device. The method comprises providing a layer comprising a continuous porous medium deposited thereon. Any porous medium previously described can be used by methods known in the art. The method also involves etching the medium to provide fluid barriers in the porous medium. The step of etching can involve physical or chemical removal of the porous media by various methods known in the art, including laser etching or chemical etching. At least a portion of the etched barriers define a capillary channel. In one embodiment, the entire portion of the barriers define a capillary channel. In another embodiment, sample applied within an application zone traverse within the barriers and the pathway constricts to a capillary channel defined by a portion of the barriers. The method also involves depositing a plurality of binding zones within the fluid barriers. Each binding zone is defined by a concentration of binding reagent immobilized on the medium. As described previously, binding reagents can be immobilized on the medium by any method known in the art.

The function and advantage of these and other embodiments of the present invention will be more fully understood from the examples below. The following examples are intended to illustrate the benefits of the present invention, but do not exemplify the full scope of the invention.

EXAMPLE 1

General Conditions

Laser Etching was performed with a 20W $CO_2$ laser from Universal Laser Systems M-20 (Scottsdale, Ariz.) equipped with 4-inch lens (beam width 0.015 inches). The procedure employed was that recommended in the manufacturer's instructions. Etching patterns were developed by means of TurboCad® software a product of IMSI (San Rafael, Calif.). Flow pathways were etched in backed nitrocellulose (no etching of the backing) at 50% power and 100% speed. When it was desired to cut through both layers the laser settings were 100% power and 50% speed Immunochemicals: Mouse monoclonal antibody to human hCG alpha subunit (M2-FO1), goat antibody to mouse immunoglobulin G (G5MG10), and colloidal gold labeled with monoclonal antibody to hCG beta subunit (M2-FO3-8) were purchased from OEM Concepts Inc. (Toms River, N.J.). Human Chorionic Gonadotropin and other chemicals employed were purchased from Sigma (St. Louis, Mo.).

Reagent dispensing was performed by means of a Biodot X-Y3000™ Dispensing Platform (Biodot Inc. Irvine Calif.), dispensing continuous lines or dots according to the manufacturer's instructions. To enhance matrix penetration, all solutions to be dispensed are diluted into 10 mM Tris buffer pH 8 with 5% ethanol.

Porous medium: Rolls of backed nitrocellulose were obtained from Millipore SRHF or from Schleicher and Schuell FF125. These are routinely stored at 40–60% relative humidity.

Reagent wicks and pads: Schleicher and Schuell 470 (Keene, N.H.) for wicks and 900 for absorbent. Prior to use the Schleicher and Schuell wicks were immersed in a solution containing 2% Bovine Serum Albumin, 0.2% Triton X-100 in 50 mM borate pH 9. These were then thoroughly dried before use.

Lamination: Components were laminated by means of G&L (San Jose, Calif.) lamination sheets (polystyrene 3" by 12') coated with GL-187 acrylic pressure sensitive adhesive and silicone release liner. The liner is back-split at 10 and 15 mm from one end and 15 mm from the other. Where indicated the release liner was split by laser etching at 100% power and 50% speed.

Conjugate release pads were prepared from QR-1 (Millipore) 8S polyester (Schleicher and Schuell), or Pecap 7-6/5 Sefar America (Depew, N.Y.) Pecap is a woven polyester with controlled pore size and thickness. 7-6/5 has pore size 6 micron and thickness and thickness of 80 micron.

Preparation of Conjugate Pads: The colloidal gold preparation at OD 40 was diluted with a solution consisting of 10 mM borate buffer pH 9.0 with 2% bovine serum albumin, 40% sucrose and 0.2% Triton X-100 to the desired final optical density. 7 mm strips of conjugate release pad of various lengths were immersed in the dilution. Excess liquid was removed by drawing the strips between latex-gloved (no talc) thumb and forefinger. These were air-dried and then held in a desiccator cabinet overnight before use. Pads are identified by the final Optical Density of the dipping solution. Thus a strip immersed in a solution with optical density of 20 is identified as an OD 20 sheet. Individual pads cut from these sheets are likewise OD 20 pads.

EXAMPLE 2

Phenomenological Demonstration of Capillarity

This example demonstrates the capillarity of laser etched channels in nitrocellulose strips. Three 4 cm by 2.5 cm rectangles of FF-125 nitrocellulose (Schleicher and Schuell) were cut out from a roll with scissors. In one of these strips, 10 lines spaced 1 mm apart were laser etched. In another strip the spacing was increased to 2 mm. The third strip served as control. The strips were dipped in water and the time required to travel 4 cm was recorded. The following rates were observed, as shown in Table 1:

TABLE 1

| Type of test strip | Time to migrate 4 cm (s) |
| --- | --- |
| Control | 132 |
| 2 mm etched lines | 86 |
| 1 mm etched lines | 56 |

EXAMPLE 3

Sheet Preparation

Diagnostic nitrocellulose strips were prepared by laser cutting from manufacturer's rolls rectangular sheets 5.5 cm by 315 cm. In most cases reagents were directly dispensed onto these sheets which were then dried either overnight at room temperature or in an oven at 45 C for 60 minutes. These were then blocked by immersion in 2% bovine serum albumin (Sigma) in 10 mM Borate pH 9. Excess liquid was removed by blotting with paper towels and the sheets were dried again as before. The desired flow pathways were then etched into these sheets.

EXAMPLE 4

Strip Preparation Sheet Lamination

G&L laminates with back-splits at 8, 10, and 65 mm from one end (hereafter the bottom end) were employed. The nitrocellulose sheets were placed in the 10 to 65 mm lane, conjugate pads were laminated at 8 mm from the bottom (5 mm overlap to nitrocellulose), pre-treated wicks 14 mm by 305 mm were layered from the bottom which covered all but 1 mm of the conjugate release strips. Where indicated, absorbent sheets (S&S 900) 20 mm by 305 mm were layered at the top. These layers were further attached by gentle rolling with a Speedball No. 71 Brayer (Hunt Manufacturing Co., Statesville, N.C.). Laser slicing of the nitrocellulose combined with razor cutting of the wick and absorbent components sliced these assemblies into individual sheets. To ensure even release of labeled binder, the release pad is held firmly against the nitrocellulose sheet by wrapping a length of quilting tape (5 mm width) around the wick, pad and polystyrene in the region where the wick overlaps the release pad.

EXAMPLE 5

Assay Performance hCG standard solutions were prepared in 10 mM borate pH 9 with 0.1% Triton X-100.1 mL of each standard was added to the rectangular wells of a pillbox. Strips were immersed in the individual wells for 5 minutes. These were then removed and visually examined for the presence of color in the various zones.

EXAMPLE 6

Tri-level Pregnancy Test

FIG. 4 depicts a strip to assess analyte concentration at three pre-determined levels. Solvent barriers were etched in a nitrocellulose sheet such that sample flowed sequentially through the application zone, the analysis zone and the reservoir zone. Solvent was allowed to pass through a first binding zone (zone 22a in the analysis zone) in a front 7 mm wide. Solvent was thereafter funneled into a capillary lane 2 mm wide. While traversing this lane, solvent passed through second (22b) and third (22c) binding zones. Not depicted is a control binding zone. Solvent emerged from the capillary channel 18 and entered the reservoir zone 16.

Reagents were dispensed into the various zones as outlined in Table 2:

TABLE 2

| Binding zone | Reagent, @concentration | Dispense |
|---|---|---|
| 1 | M2-F01, 1.5 mg./ml. | Line 1.1 µl./cm. |
| 2 | M2-F01, 0.8 mg/ml | Dot .312 µl |
| 3 | M2-F01, 0.6 mg/ml. | Dot .312 µl |
| control | G5-MG10, 1.0 mg./ml | Dot .312 µl |

These reagent quantities were dispensed onto pre-etched sheets or dispensed on plain sheets that were etched after blocking and drying. (See Examples 1 and 2 for etching procedures.)

Table 3 shows the results of samples applied to the pre-etched sheets, in which the samples contained known concentrations of hCG of 0, 50, 1000, 2500, 5000, 10,000, 20,000 and 50,000 mIU/mL. After 5 minutes the individual sheets were examined and graded for color development in each of the zones.

TABLE 3

| hCG mIU/mL in sample | Binding Zone 1 | Binding Zone 2 | Binding Zone 3 | Control Zone |
|---|---|---|---|---|
| 0 | − | − | − | + |
| 50 | + | − | − | + |
| 1000 | + | − | − | + |
| 2500 | + | − | − | + |
| 5000 | + | + | − | + |
| 10,000 | + | + | − | + |

TABLE 3-continued

| hCG mIU/mL in sample | Binding Zone 1 | Binding Zone 2 | Binding Zone 3 | Control Zone |
|---|---|---|---|---|
| 20,000 | + | + | + | + |
| 50,000 | + | + | + | + |

It can be seen that samples having lower concentrations were capable of producing a detectable signal in binding zone one only. Intermediate concentrations were capable of producing a detectable signal in binding zones one and two whereas samples having high concentrations of hCG were capable of producing a detectable signal in all three binding zones. Thus, this specific example is designed if a user needs to know whether a sample contains particular threshold concentrations, and of course concentrations of reagents in the binding zones can be varied for detecting different threshold concentrations. The positive result of all the samples in the control zone indicates that the sheets are capable of producing a detectable signal.

Those skilled in the art would readily appreciate that all parameters listed herein are meant to be examples and that actual parameters will depend upon the specific application for which the methods and apparatus of the present invention are used. It is, therefore, to be understood that the foregoing embodiments are presented by way of example only and that, within the scope of the appended claims and equivalents thereto, the invention may be practiced otherwise than as specifically described.

What is claimed:

1. A device for determining the presence of an analyte, comprising:
   a layer including a continuous porous medium deposited thereon;
   a fluid pathway defined by fluid barriers in the porous medium, at least a portion of the barriers defining a capillary channel;
   an analysis zone within the fluid pathway comprising a plurality of binding zones for binding and immobilizing the analyte, each binding zone being defined by a concentration of a binding reagent immobilized on the medium; and
   an application zone at a first end of the fluid pathway and upstream of the analysis zone, for receiving a sample suspected of containing an analyte,
   wherein the fluid pathway comprises a constriction region immediately upstream of the capillary channel, for constricting and directing fluid flow to the capillary channel.

2. The device of claim 1, wherein the application zone further comprises a wick positioned against the first end of the layer.

3. The device of claim 2, wherein the application zone further comprises a labeling agent intermediate and adjacent the wick and the analysis zone.

4. The device of claim 3, wherein the labeling agent is a visual labeling agent.

5. The device of claim 4, wherein the labeling agent comprises colloidal gold.

6. The device of claim 1, wherein the constriction region is tapered.

7. The device of claim 1, wherein the capillary channel has a width of less than about 4 mm.

8. The device of claim 1, wherein the capillary channel has a width of less than about 3 mm.

9. The device of claim 1, wherein the capillary channel has a width of less than about 2 mm.

10. The device of claim 1, wherein the porous medium is a nitrocellulose.

11. The device of claim 1, wherein the porous medium has a thickness from about 10 µm to about 400 µm.

12. The device of claim 11, wherein the porous medium has a thickness from about 100 µm to about 200 µm.

13. The device of claim 1, wherein the porous medium includes pores having a mean average diameter from about 0.45 µm to about 50 µm.

14. The device of claim 1, wherein at least one of the binding zones is positioned within the capillary channel.

15. The device of claim 1, wherein each binding zone spans the width of the fluid pathway.

16. The device of claim 1, wherein the plurality of binding zones comprises at least two binding zones.

17. The device of claim 1, wherein the binding zones are analysis zones which further comprise a labeling agent for detecting bound analyte.

18. The device of claim 17, further comprising an adjuster zone positioned between two binding zones, for filtering out a defined amount of analyte.

19. The device of claim 1, wherein the binding agent is an antibody.

20. The device of claim 1, wherein the binding agent is selected from the group consisting of avidin and streptavidin.

21. The device of claim 1, further comprising a control binding zone positioned on the layer and outside of the analysis zone.

22. The device of claim 21, further comprising a defined amount of analyte positioned upstream of the control binding zone.

23. The device of claim 1, wherein the device comprises a kit for medical diagnosis.

24. The device of claim 23, wherein the device is a component of a pregnancy test kit.

25. The device of claim 23, wherein the device is a component of a prostrate cancer test.

26. The device of claim 1, wherein the device is capable of detecting an amount of analyte.

27. The device of claim 1, wherein the device comprises an immunoassay device.

28. A device for determining the presence of an analyte, comprising:
   a layer including a continuous porous medium deposited thereon;
   a fluid pathway defined by fluid barriers in the porous medium, at least a portion of the barriers defining a capillary channel; and
   an analysis zone within the fluid pathway comprising a plurality of binding zones for binding and immobilizing the analyte, each binding zone being defined by a concentration of a binding reagent immobilized on the medium, wherein the fluid barriers are screen-printed barriers.

29. A device for determining the presence of an analyte, comprising:
   a layer including a continuous porous medium deposited thereon;
   a fluid pathway defined by fluid barriers in the porous medium, at least a portion of the barriers defining a capillary channel; and
   an analysis zone within the fluid pathway comprising a plurality of binding zones for binding and immobilizing the analyte, each binding zone being defined by a concentration of a binding reagent immobilized on the medium, wherein the fluid barriers are etched barriers.

30. The device of claim 29, wherein the etched barriers are a laser-etched barriers.

31. The device of claim 29, wherein the etched barriers are chemically-etched barriers.

32. A device for determining the presence of an analyte, comprising:
   a layer including a continuous porous medium deposited thereon;
   a fluid pathway defined by fluid barriers in the porous medium, at least a portion of the barriers defining a capillary channel; and
   an analysis zone within the fluid pathway comprising a plurality of binding zones for binding and immobilizing the analyte, each binding zone being defined by a concentration of a binding reagent immobilized on the medium, wherein the fluid barriers are serrated barriers.

33. A device for determining the presence of an analyte, comprising:
   a layer including a continuous porous medium deposited thereon;
   a fluid pathway defined by fluid barriers in the porous medium, at least a portion of the barriers defining a capillary channel; and
   an analysis zone within the fluid pathway comprising a plurality of binding zones for binding and immobilizing the analyte, each binding zone being defined by a concentration of a binding reagent immobilized on the medium, wherein the fluid barriers are defined by edges of the layer.

34. A device for determining the presence of an analyte, comprising:
   a layer including a continuous porous medium deposited thereon;
   a fluid pathway defined by fluid barriers in the porous medium, at least a portion of the barriers defining a capillary channel;
   an analysis zone within the fluid pathway comprising a plurality of binding zones for binding and immobilizing the analyte, each binding zone being defined by a concentration of a binding reagent immobilized on the medium; and
   a reservoir zone at a second end of the fluid pathway and upstream of the analysis zone, to facilitate removal of fluid from the analysis zone, wherein the reservoir zone comprises a series of capillary channels in parallel arrangement with each other, each capillary channel being contiguous with the fluid pathway.

35. The device of claim 34, wherein the reservoir zone comprises an absorbent.

36. A device for determining the presence of an analyte, comprising:
   a layer including a continuous porous medium deposited thereon;
   a fluid pathway defined by fluid barriers in the porous medium, at least a portion of the barriers defining a capillary channel; and
   an analysis zone within the fluid pathway comprising a plurality of binding zones for binding and immobilizing the analyte, each binding zone being defined by a concentration of a binding reagent immobilized on the medium,
   wherein the plurality of binding zones is arranged substantially linearly and sequentially with respect to a direction of fluid flow, and a concentration of binding agent in the binding zones decreases successively in the direction of fluid flow.

37. The device of claim 36, wherein each binding zone has an equal concentration of binding agent immobilized on the porous medium.

38. The device of claim 37, wherein a first binding agent in a first binding zone has a different binding strength than that of a second binding agent in a second binding zone.

39. A device for determining the presence of an analyte, comprising:

a layer including a continuous porous medium deposited thereon;

a fluid pathway defined by fluid barriers in the porous medium, at least a portion of the barriers defining a capillary channel; and an analysis zone within the fluid pathway comprising a plurality of binding zones for binding and immobilizing the analyte, each binding zone being defined by a concentration of a binding reagent immobilized on the medium, wherein the concentration of binding reagent immobilized on the medium defines a maximum threshold detection level.

* * * * *